(12) United States Patent
Meyer et al.

(10) Patent No.: US 6,576,022 B2
(45) Date of Patent: Jun. 10, 2003

(54) ADJUSTABLE CONNECTOR ASSEMBLY FOR A PROSTHETIC LIMB

(75) Inventors: Wilbur N. Meyer, Brookville, OH (US); Robert B. Meyer, Lewisburg, OH (US)

(73) Assignee: Bulldog Tools Inc., Lewisburg, OH (US)

( * ) Notice: Subject to any disclaimer, the term of this patent is extended or adjusted under 35 U.S.C. 154(b) by 0 days.

(21) Appl. No.: 10/103,014

(22) Filed: Mar. 22, 2002

(65) Prior Publication Data

US 2003/0065403 A1 Apr. 3, 2003

Related U.S. Application Data

(63) Continuation-in-part of application No. 29/149,013, filed on Oct. 1, 2001, now Pat. No. Des. 462,767, and a continuation-in-part of application No. 29/149,014, filed on Oct. 1, 2001, now Pat. No. Des. 462,768.

(51) Int. Cl.[7] .................................................. A61F 2/62
(52) U.S. Cl. ............................................ 623/38; 403/4
(58) Field of Search ................................ 623/38; 403/3, 403/4

(56) References Cited

U.S. PATENT DOCUMENTS

| | | | | |
|---|---|---|---|---|
| 5,137,290 A | * | 8/1992 | Patterson et al. | ............ 403/4 X |
| 6,013,105 A | | 1/2000 | Potts | |
| 6,033,440 A | | 3/2000 | Schall et al. | |
| 6,106,559 A | | 8/2000 | Meyer | |
| 6,228,124 B1 | * | 5/2001 | Slemker et al. | ................ 623/47 |

* cited by examiner

*Primary Examiner*—David H. Willse
(74) *Attorney, Agent, or Firm*—Jacox, Meckstroth & Jenkins

(57) ABSTRACT

An adjustable connector assembly includes a circular one-piece base member adapted to be attached to a socket coupler for an amputee's residual limb. The base member has axially projecting spaced track portions which receive therebetween a circular flange of a slidable and rotatable one-piece connector member. A pair of clamping plates receive screws threaded into the track portions for releasably clamping the flange to the base member. In one embodiment, the connector member has a dome surface and a four sided boss projecting from the flange. In another embodiment, the connector member has a projecting annular collar having peripherally spaced threaded holes. The base member and connector member are adapted to be machined from solid titanium bar stock.

19 Claims, 2 Drawing Sheets

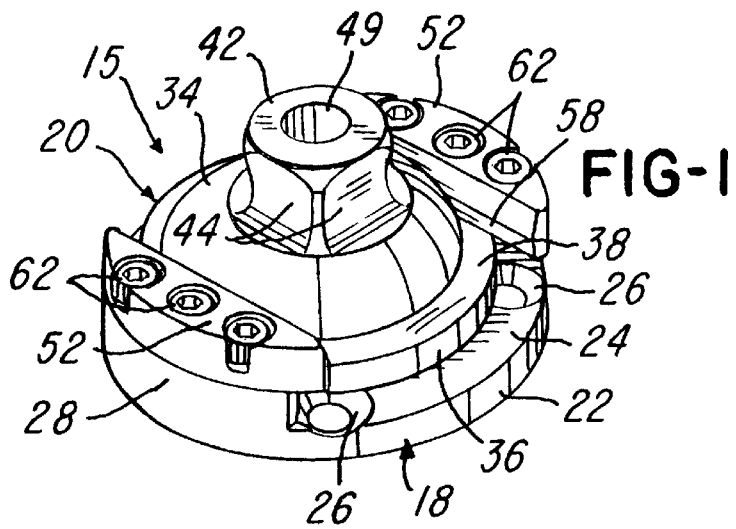
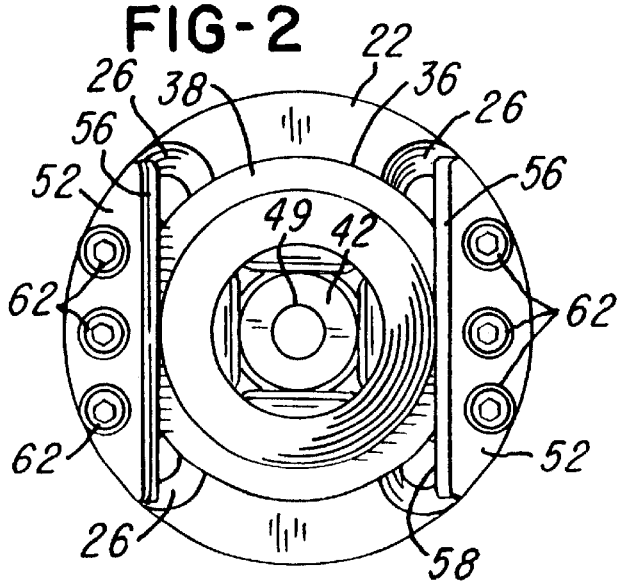
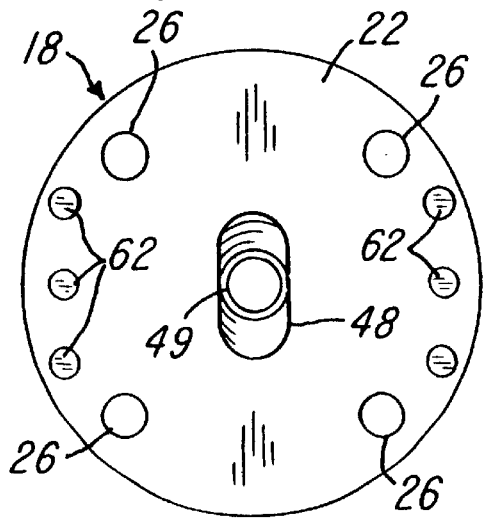
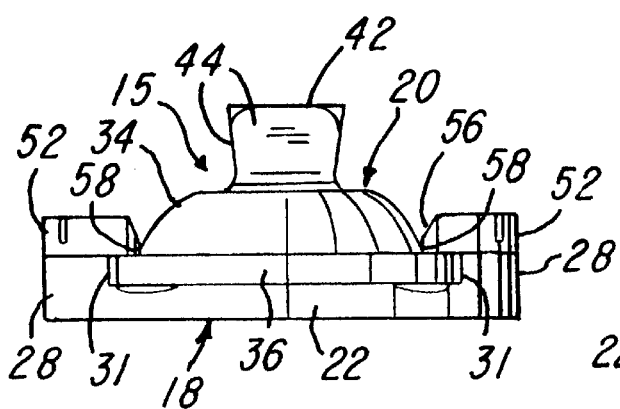
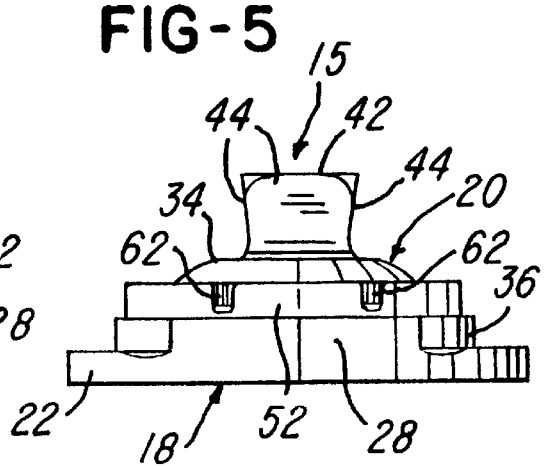

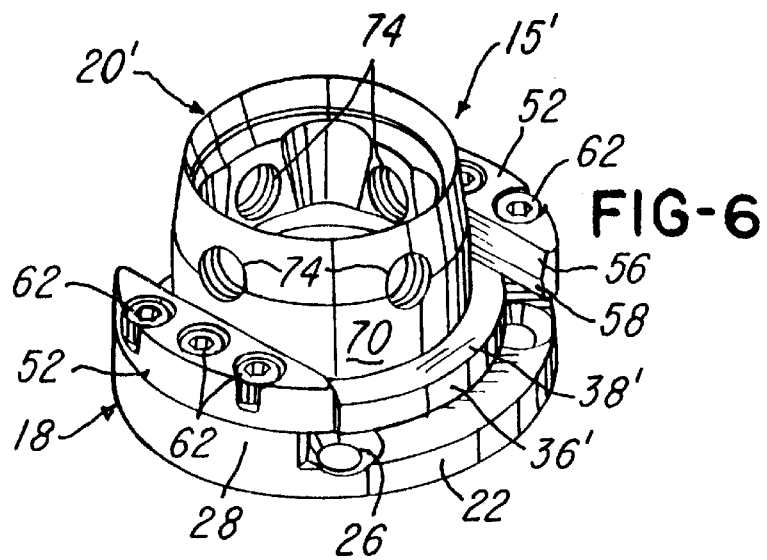
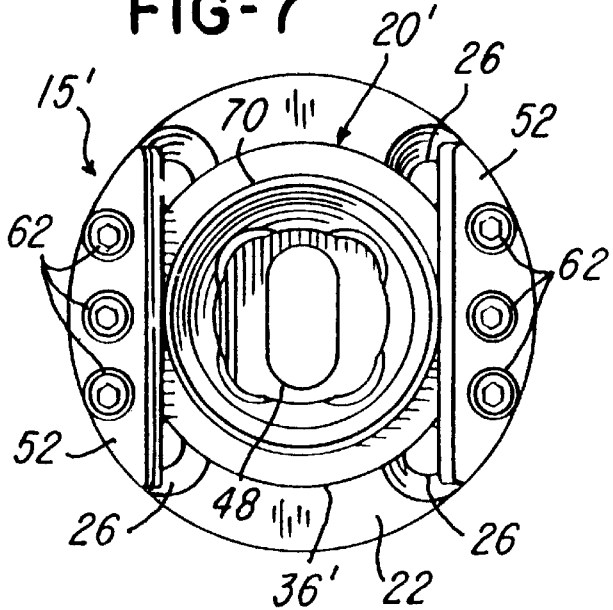
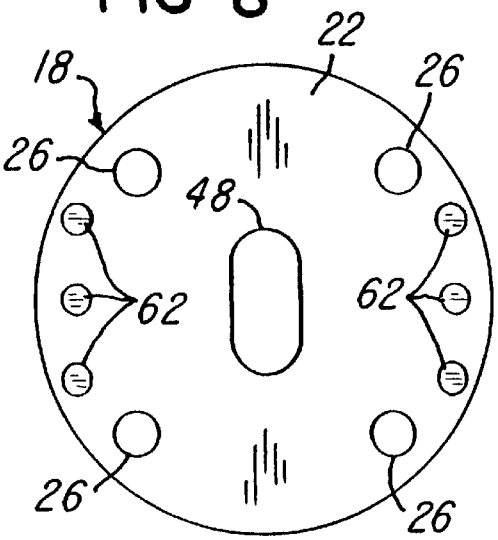
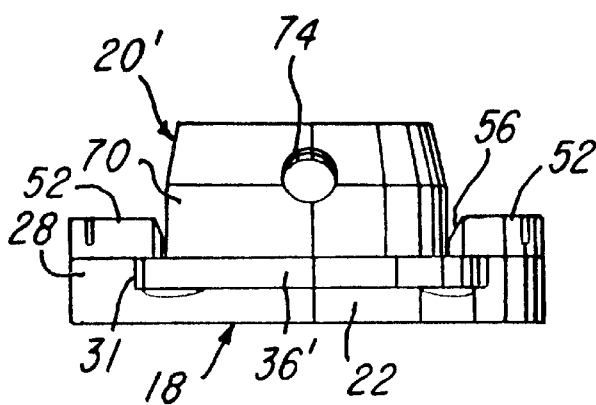
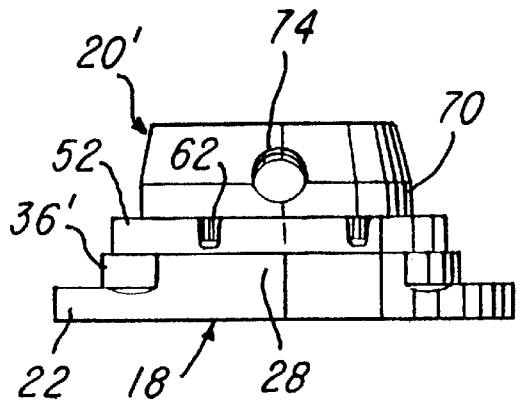

ADJUSTABLE CONNECTOR ASSEMBLY FOR A PROSTHETIC LIMB

This application is a continuation-in-part of U.S. Design patent application Ser. No. 29/149,013, filed on Oct. 1, 2001, now U.S. Design Pat. No. D462,767 S, and is a continuation-in-part of U.S. Design patent application Ser. No. 29/149,014, filed on Oct. 1, 2001, now U.S. Design Pat. No. D462,768 S.

BACKGROUND OF THE INVENTION

The present invention relates to an adjustable connector assembly for a prosthetic limb, for example, of the general type disclosed in U.S. Pat. No. 6,033,440, the disclosure of which is incorporated by reference. FIGS. 1A and 1B of this patent disclose a conventional pyramidal boss connector or link plate 10, and a similar pyramidal connector or bracket 55 is disclosed in FIGS. 1 & 4 of U.S. Pat. No. 6,106,559 which is assigned to the assignee of the present invention. FIGS. 2–10 of above-mentioned U.S. Pat. No. 6,033,440 disclose an adjustable pyramidal link plate assembly which incorporates a rotatable four sided boss wedged within a slide confined within a dovetail slot held by laterally projecting set screws. The assembly is adapted to be used when a prosthetic leg is not properly aligned with an amputee's residual limb or stump and provides for lateral adjustment as well as rotatable adjustment of the artificial leg relative to the stump and socket. Another form of adjustable pyramid connector is disclosed in U.S. Pat. No. 6,013,105. This connector also provides for sliding and rotating the pyramidal boss with the use of a an undercut slot and a central locking screw extending through the boss into a nut slidable with the slot.

SUMMARY OF THE INVENTION

The present invention is directed to an improved adjustable connector assembly for a prosthetic limb and which also provides for lateral and rotational adjustment. In addition, the adjustable connector assembly of the invention provides for substantial strength and rigidity after adjustment. In one form, the connector has a projecting four sided pyramidal boss and in another form, has an annular collar for receiving such a boss. The connector assembly of the invention may also be efficiently and economically constructed from solid titanium bar stock on a numerically controlled machine tool in order to provide the assembly with compactness and low weight in addition to high strength.

In accordance with a preferred embodiment of the invention, a circular base member or plate is formed with a flat base surface and a pair of generally parallel spaced and integral track portions. Countersink holes are formed from the base surface through the base plate for attaching the base plate, for example, to a coupler mounted within the bottom portion of a socket which receives the residual limb portion. A circular connector member has an outwardly projecting circular base flange which fits between the track portions of the base plate, and the base flange is rigidly secured or clamped to the base plate by a pair of opposing clamping rails each of which is secured to the base plate by a set of socket head machine screws extending into the corresponding track portion.

In one embodiment, the connector member has a dome surface projecting from the base flange and a projecting four sided pyramidal boss with undercut surfaces for engagement by the ends of set screws extending, for example, through threaded holes within an annular adaptor for a prosthetic leg pylon. In another embodiment, the connector member includes an annular collar projecting from the annular base flange for receiving a four sided pyramidal boss. The collar has circumferentially-spaced threaded holes through which set screws extend for engaging the undercut surfaces of the pyramidal boss.

Other features and advantages of the invention will be apparent from the following description, the accompanying drawings and the appended claims.

BRIEF DESCRIPTION OF THE DRAWINGS

FIG. 1 is a perspective view of one embodiment of an adjustable coupler or connector assembly constructed in accordance with the invention for a prosthetic leg;

FIG. 2 is a top view of the connector assembly shown in FIG. 1;

FIG. 3 is a bottom view of the connector assembly shown in FIG. 1;

FIGS. 4 & 5 are end and side views of the connector assembly shown in FIG. 1;

FIG. 6 is a perspective view of an adjustable coupler or connector assembly constructed in accordance with another embodiment of the invention; and FIGS. 7–10 are top, bottom, end and side views of the connector assembly shown in FIG. 6.

DESCRIPTION OF THE PREFERRED EMBODIMENTS

Referring to FIG. 1, an adjustable connector assembly 15 includes a base member 18 and a connector member 20 both of which have components machined from solid titanium bar stock. The base member 18 includes a circular base plate portion 22 having a generally flat upper surface 24, and a set of four countersink holes 26 extending through the plate portion 22 and adapted to receive flat head screws for securing the base member 18 to a socket and coupler as disclosed in above-mentioned U.S. Pat. No. 6,106,559. The base member 18 includes a pair of generally parallel spaced track portions 28 which are integrally connected by the plate portion 22 and have parallel spaced and opposing flat inner surfaces 31 (FIG. 4).

The connector member 20 includes a hollow dome portion 34 from which extends a bottom annular flange 36 having a diameter slightly less than the space in between the opposing parallel surfaces 31 on the base member 18. The flange 36 has a substantially flat top annular surface 38 which extends outwardly from the dome portion 34. The connector member 20 also includes an axially or upwardly projecting four sided annular boss 42 having peripherally spaced undercut surfaces 44 which are adapted to receive the inner ends of inclined attachment screws such as the screws extending through an annular or tubular adaptor seated on the dome portion 34, as disclosed in FIG. 3 of above-mentioned U.S. Pat. No. 6,231,618. The plate portion 22 of the base member 18 is formed with a slot 48 which extends parallel to the track surfaces 31 and is aligned with a center hole 49 formed within the boss 42 of the connector member 20. The hole 49 and slot 48 are adapted to receive the end portion of an elongated locking stud which projects through the coupler located in the lower end portion of the socket, for example, as shown in above-mentioned U.S. Pat. No. 6,106,559.

The height of the track portions 28 and inner surfaces 31 is substantially the same or a few thousands less than the thickness of the flange 36 of the connector member 20. As apparent from FIGS. 1, 2 & 4, the flange 36 is positively clamped and secured to the flat surface 24 of the base member 18 by a pair of parallel spaced clamping bars or members 52 which seat on the top end surfaces of the track portions 28. Each of the clamping members or bars 52 has a part-circular outer surface which conforms with the outer surface of the base member 18 and a linear inner beveled surface 56 with extends from an inner flat surface 58. The spacing between the parallel spaced inner surfaces 58 is slightly greater than the diameter of the dome portion 34 adjacent the flange 36 and form a linear guide or track for sliding the connector member 20 laterally on top of the surface 24.

A set of three socket head machine screws 62 have head portions recessed within counterbores in each of the clamping members or bars 52 and extend into corresponding threaded holes formed within the base member 18. When the screws 62 are loosened, the connector member 20 is free to rotate and slide between the clamping elements 52 by predetermined distance, for example, plus or minus ½ inch from the center position shown in FIG. 2. When the screws 62 are tightened with the aid of an Allen wrench, the flange portion 36 of the connector member 20 is rigidly secured and clamped to the base member 18 so that the connector member 20 and base member 18 are positively locked together and will not vibrate apart as a result of extensive walking with the artificial leg.

FIGS. 6–10 show another embodiment of an adjustable connector assembly 15' which is adapted to receive a pyramidal boss such as the four sided boss 42 described above in connection with FIGS. 1–5. The assembly 15' uses the same base member 18 and clamp members 52 as described above for the assembly 15 and therefore has the same reference numbers for the same structural components. In the assembly 15', the connector member 20' includes an annular collar 70 having an outwardly projecting cylindrical base flange 36' which seats on the base surface 24 of the base member 18. The diameter of the annular collar 70 adjacent the flange 36' is slightly less than the spacing between the parallel surfaces 58 of the clamping members 52 so that the connector member 20' is free to rotate and slide laterally on the surface 24 when the screws 62 are released. The collar 70 also has four circumferentially spaced threaded holes 74 which are slightly inclined inwardly and downwardly for receiving corresponding set screws. The set screws are adapted to connect the collar 70 to a four sided pyramidal boss which may be secured, for example, to the upper end portion of a tubular pylon of an artificial leg. The rotary and laterally sliding adjustment of the connector assembly 15' is performed in the same manner as described above for the connector assembly 15.

From the drawings and the above description, it is apparent that a connector assembly constructed in accordance with the present invention, provides desirable features and advantages. For example, each of the components of the connector assembly 20 or 20' is adapted to be machined from solid titanium bar stock with a CNC machine tool, thus providing for not only high strength, but compactness and low weight. As another advantage, when the clamping bars or members 52 are secured by the screws 62 to the base member 18, the outwardly projecting flange 36' is firmly and positively clamped and reliably connected to the base member 18. As a result, the connector assembly will not become loose after it has been in use for an extended period of time. As another feature, the base member 18 may be used with either the pyramidal boss connector 20 or the boss receiver connector 20', depending upon the requirements of the prosthetic leg.

While the forms of connector assembly herein described constitute preferred embodiments of the invention, it is to be understood that the invention is not limited to these precise forms, and that changes may be made therein without departing from the scope and spirit of the invention as defined in the appended claims.

What is claimed is:

1. An adjustable connector assembly for a prosthetic leg member, comprising a base member adapted to be attached to a socket coupler and having a generally flat base surface, a connector member supported by said base surface and having a laterally outwardly projecting flange supported by said base surface, a set of spaced clamping members disposed on opposite sides of said connector member above said flange, a set of screws securing said clamping members to said base member, and said connector member and said flange being free to rotate and slide laterally between said clamping members and relative to said base surface when said screws are released.

2. An assembly as defined in claim 1 wherein said connector member includes a dome portion projecting from said flange, and a multi-sided boss projecting from said dome portion and having a plurality of peripherally spaced undercut surfaces adapted to be engaged by attachment screws.

3. An assembly as defined in claim 1 where said connector member includes an annular portion projecting from said flange and having peripherally spaced threaded holes adapted to receive corresponding attachment screws.

4. An assembly as defined in claim 1 where said base member comprises a set of generally parallel spaced track portions integrally connected by a plate portion with said track portions projecting from said base surface, and said screws extend through said clamping members and are threaded into said track portions.

5. An assembly as defined in claim 1 wherein each of said clamping members has a curved outer surface and a generally straight inner surface, and a plurality of said screws extend through each of said clamping members and into said base member.

6. An assembly as defined in claim 1 wherein said flange on said connector member is circular and has a substantially flat top annular surface engaged by said clamping members.

7. An assembly as defined in claim 1 wherein said base member and said connector member are each circular, and said flange on said connector member has a substantially flat top annular surface extending under said clamping members.

8. An assembly as defined in claim 1 wherein said base member is circular and has a centrally located slot extending generally parallel to said clamping members and adapted to receive a locking stud projecting through the socket coupler.

9. An adjustable connector assembly for a prosthetic leg member, comprising a circular base member adapted to be attached to a socket coupler and having a generally flat base surface, a circular connector member supported by said base surface and having a laterally outwardly projecting annular flange supported by said base surface, a set of spaced clamping members disposed on opposite sides of said connector member above said flange, a set of screws securing each of said clamping members to said base member, and said connector member and said flange being free to rotate and slide laterally between said clamping members and relative to said base surface when said screws are released.

10. An assembly as defined in claim 9 wherein said connector member includes a dome portion projecting from said flange, and a multi-sided boss projecting from said dome portion and having a plurality of peripherally spaced undercut surfaces adapted to be engaged by attachment screws.

11. An assembly as defined in claim 9 where said connector member includes an annular body portion projecting from said flange and having peripherally spaced threaded holes adapted to receive corresponding attachment screws.

12. An assembly as defined in claim 9 where said base member comprises a set of generally parallel spaced track portions integrally connected by a plate portion with said track portions projecting from said base surface, and said screws extend through said clamping members and are threaded into said track portions.

13. An assembly as defined in claim 9 wherein each of said clamping members has a generally straight inner surface and a part circular outer surface flush with an outer surface of said base member, and a plurality of said screws extend through each of said clamping members and into said base member.

14. An assembly as defined in claim 9 wherein said flange on said connector member has a flat top annular surface engaged by said clamping members.

15. An assembly as defined in claim 9 wherein said base member has a centrally located slot extending generally parallel to said clamping members and adapted to receive a locking stud projecting through the socket coupler.

16. An assembly as defined in claim 9 wherein said base member and said connector member each comprise a one-piece titanium body.

17. An adjustable connector assembly for a prosthetic leg member, comprising a one-piece titanium base member adapted to be attached to a socket coupler and having a generally flat base surface, a one-piece titanium connector member supported by said base surface and having a laterally outwardly projecting annular flange supported by said base surface, a pair of spaced titanium clamping members disposed on opposite sides of said connector member above said flange, each of said clamping members having the shape of a segment of a circle, a plurality of screws securing each of said clamping members to said base member, and said connector member and said flange being free to rotate and slide laterally between said clamping members and relative to said base surface when said screws are released.

18. An assembly as defined in claim 17 wherein said connector member includes a dome portion projecting from said flange, and a multi-sided boss projecting from said dome portion and having a plurality of peripherally spaced undercut surfaces adapted to be engaged by attachment screws.

19. An assembly as defined in claim 17 where said connector member includes an annular body portion projecting from said flange and having peripherally spaced threaded holes adapted to receive corresponding attachment screws.

* * * * *